United States Patent [19]

Kirsch

[11] Patent Number: 5,102,414

[45] Date of Patent: Apr. 7, 1992

[54] IMPLANTABLE FIXING DEVICE FOR EXTRAORAL APPLICATIONS

[75] Inventor: Axel Kirsch, Filderstadt, Fed. Rep. of Germany

[73] Assignee: IMZ Fertigungs-und Vertriebsgesellschaft für dentale Technologie mbH, Fed. Rep. of Germany

[21] Appl. No.: 447,641

[22] Filed: Dec. 8, 1989

[30] Foreign Application Priority Data

Dec. 10, 1988 [DE] Fed. Rep. of Germany ....... 3841704

[51] Int. Cl.⁵ ............................................. A61B 17/58
[52] U.S. Cl. ..................... 606/73; 606/187; 606/53; 623/13
[58] Field of Search ............ 606/53, 73, 130, 187; 623/13, 15; 132/53, 201

[56] References Cited

U.S. PATENT DOCUMENTS

| 1,526,182 | 2/1925 | Rosenberg | 606/72 |
| 3,862,453 | 1/1975 | Widdifield | 623/15 |
| 4,793,808 | 12/1988 | Kirsch . | |
| 4,870,957 | 10/1989 | Goble et al. | 606/73 |
| 4,963,144 | 10/1990 | Huene | 606/72 |

FOREIGN PATENT DOCUMENTS

| 0170358 | 2/1986 | European Pat. Off. . |
| 0238223A2 | 9/1987 | European Pat. Off. . |
| 0260787 | 3/1988 | European Pat. Off. . |
| 0260970A2 | 3/1988 | European Pat. Off. . |
| 0279129 | 8/1988 | European Pat. Off. . |
| 1961531 | 7/1970 | Fed. Rep. of Germany . |
| 2628443 | 5/1985 | Fed. Rep. of Germany . |
| 3735378 | 7/1988 | Fed. Rep. of Germany . |
| 3800368 | 7/1988 | Fed. Rep. of Germany . |
| 0739089 | 1/1933 | France ................................ 606/73 |
| 89/09030 | 10/1989 | World Int. Prop. O. ........... 606/73 |

OTHER PUBLICATIONS

Union Carbide Advertisement, 1953.
Amis, "The Strength of Artificial Ligament Anchorages", *The Journal of Bone and Joint Surgery*, vol. 70-B, No. 3, May 1988, pp. 397–403.

Primary Examiner—Stephen C. Pellegrino
Assistant Examiner—Michael Rafa
Attorney, Agent, or Firm—Hill, Van Santen, Steadman & Simpson

[57] ABSTRACT

An implantable fixing device for extraoral applications includes a basic structure implantable in the bone and having either a thread-pressing or a thread-cutting helix, and an implant post being connectible to the basic structure by being inserted in an axial bore therein.

24 Claims, 1 Drawing Sheet

IMPLANTABLE FIXING DEVICE FOR EXTRAORAL APPLICATIONS

BACKGROUND OF THE INVENTION

The present invention is directed to an implantable fixing means for extraoral applications.

For many years now, implantations have taken place of artificial ligaments, which link the parts of a human skeleton which are movable relative to one another. For example, in the case of damage or chronic instability of the crucial ligaments of the knee joint and when an intra-articular autologous reconstructions fails, it is possible to implant a set of crucial ligaments made from synthetic material. A special polytetrafluorethylene, which is sold under the trade name GORE-TEX, has proved suitable for this purpose because it is biologically inert and, therefore, particularly compatible with the body.

It has long been assumed that the fixing means for such artificial ligaments only plays a minor part because over the course of time they grow together with the endogenic tissue. However, it was found a certain time ago that the tissue reaction to the implantable crucial ligament sets differs widely so that it is not possible in all cases to assume a reliable growth of the artificial ligament into the endogenic tissue (See Ruston N. Dandy DJ, Naylor CPE. "The clinical, arthroscopic and histological findings after replacement of the anterior cruciate ligament with carbon-fibre". *J. Bone Joint Surg* (Br) 1983: 65-B: 308-9.) Thus, in many cases, the fixing means must fulfill their function for a long time in order, for example, to be able to withstand large forces which, even in the case of normal movement sequences, occurs in the knee joint.

Literature and practice provide numerous proposals for fixing or fastening of artificial ligaments. Apart from the conventional Sherman, special cortical screws have been developed for specific fixing loops. In addition, Richards clamps are used which may have barbs for insuring reliable seating in the previously-drilled bone. Bollard-like fixing means made from carbon fibre/polysulphone material have a split shank which is spread apart by knocking in a median pin. In addition, special implantable fixing members and in conjunction with cortical screws special through sleeves have been proposed (See article by Andrew A. Amis, "The strength of artificial ligament anchorages", J. Bone Joint Surg (Br) 1988: 70-B: 397-403).

Hitherto known fixing means for artificial ligaments are either very complicated with regard to their implantation or are not sufficiently stable to permanently withstand, without damage, the extremely high forces which can, for example, occur in the vicinity of the knee joint. Thus, there are constant deformations or even breaks in the fastening means or damage to the surrounding bone material which, in each case, makes further surgery necessary.

However, the fixing means for extraoral applications are not only required for artificial ligaments, but also in other fields.

In the case of serious cutaneous lesions, such as, for example, serious burns, it is necessary, for the avoidance of infection, to immediately cover the affected area with the suitable material. Particular problems are encountered with respect to a rapid and reliable fixing of the covering material because the destroyed areas are particularly sensitive to pressure and pain and, simultaneously, can have a marked plasticity and small surface area, for example in the facial area. No practical solution has heretofore been made for solving these problems.

SUMMARY OF THE INVENTION

The object of the present invention is to therefore provide a rapid and reliable implantation fixing device or means for extraoral applications. These fixing devices are particularly for fixing artificial ligaments and covering materials for injuries. According to this invention, this problem is solved by providing an implantable fixing device for extraoral applications comprising a basic or base structure implantable in the bone and having an external helix, said base structure having a bore and an implantable implant post being connectible to the basic structure by being inserted in said bore. The helix can either be a thread cutting helix or a pressing helix.

As a result of the thread pressing or cutting helix of the basic structure, it is possible to rapidly and reliably implant the inventive fixing device in any conceivable bone material. In the case of an at least equivalent stability compared with known fixing means, it is particularly advantageous that the forces exerted over the fixed object, such as, for example, the artificial ligament, have scarcely any action on the implanted basic structure. This force takes place most exclusively on the implant post inserted in the base structure. The implant post can be easily and rapidly replaced if the above-mentioned deformation or breakage occurs without surgery being necessary.

When used as a fixing means or device for the covering material for injuries, the basic structure, according to the invention, can be particularly easily implanted in the head area, because at many points a bone is directly beneath the skin so that it is scarcely necessary to destroy muscle tissue during implantation. The inventive fixing means can be rapidly and reliably fitted around the destroyed or injured area and can then be used for fixing the necessary covering material.

The fixing means or device according to the invention is obviously not limited to the uses described hereinbefore and can also be used for fixing random materials to bones. Thus, for example, it is also possible to fix hair transplants in this manner.

In order to insure an optimum anchoring of the basic or base structure in the bone material, the helix is located in the vicinity of its upper edge or end. The invention proposes that the helix extends over a maximum of 1.5 or not more than 1.5 revolutions and, preferably, in a range of 1-1.25 revolutions around the basic structure and has a pitch or lead between 1 and 2 and, in a particularly preferred manner, a lead or pitch of 1.5. With such a coil or helix construction, it is possible to reliably anchor the basic structure in the bone material without having to provide a thread over the entire length of the base structure. When used as a fixing means for the covering material of injuries, the basic structure can even end shortly below the helix, for example it can be kept relatively short and can, therefore, be particularly rapidly, but still reliably, turned into the bone material. This permits a reliable seating of the basic structure in the bone material without having to penetrate too deeply.

The helix can have sides forming an angle of approximately 60° or, when used in particularly sensitive bone areas, such as in the head area, where a sharp-edged helix or coil could easily lead to tearing or flaking, can have a rounded structure.

A particularly favorable material for the basic structure, due to its limited susceptibility to body fluids and its high stability with respect to tensile forces, is a metal selected from the group consisting of titanium and titanium alloys.

Advantageously, the basic structure is externally coated with a tissue-friendly material. A plasma coating of hydroxyl apatite has proved most suitable for this. This material, which is inter alia also the main constituent of dental enamel, reliably avoids rejection reactions of the tissue surrounding the basic structure.

So that the basic structure can be screwed as simply and reliably as possible into the bone material and, if necessary, can be removed again therefrom, it has proved advantageous to provide, on the upper end face of the basic structure, radially extending blind bores for the engagement of a corresponding special type wrench.

In order to prevent an unintended, excessively deep penetration of the basic structure into the bone material, which is particularly important in the case of sensitive bone regions, according to the present invention, the basic structure has a widened, upper marginal area or flange.

According to an advantageous embodiment of the invention, a spacer sleeve is provided which can be mounted on the upper edge of the basic structure as an extension. A particular advantage of this spacer sleeve is that it is able to rigidly extend the basic structure, which initially is consolidated into the bone under the reclosing skin, over the upper edge thereof, without any irritation being caused by deformable movement. Advantageously, the spacer sleeve is made from an electrically insulating material. For this purpose, it is particularly possible to use a ceramic material, such as a ceramic material selected from a group consisting of aluminum oxide, magnesium oxide, zirconium dioxide and combinations of aluminum oxide, magnesium oxide and zirconium dioxide. Such a material will insure an optimum skin compatibility for the spacer sleeve. With regard to the design of the spacer sleeve, it has proved advantageous for the upper surface of the basic structure to have a countersinked portion around the bore and the spacer sleeve to have a conical protrusion or cone on one end for engagement in the countersink. This structure will insure a powerful frictional and positive connection of the two parts.

The implant post to be inserted in the basic structure can be connectible thereto in a screwable or bayonet-like fashion. For a simple and rapid fitting of the implant post, the invention provides for the location on its upper end face with radially extending blind bores for the engagement of a corresponding special wrench.

The fixing of the artificial ligament, covering material for injuries and optionally other materials can take place in different ways. Thus, it is possible to provide in the material to be fixed holes or rows of holes into which are engaged on the implant post. According to an embodiment of the invention, the implant post has fixing means for engaging or attaching material which means may be a widened head which engages over and fixes the material to be fixed after insertion of the implant post through one of the fixing holes. However, according to another embodiment of the invention, the fixing means can be brought about by one or more hooks on the top of the implant post. When fixing artificial ligaments, the corresponding fiber bundle can be fused or melted to rectangular attachment pieces into which have been melted corresponding shaped implant posts. In order to be able to carry out a corresponding length adaptation of the artificial ligament, it is advantageous to have several rows of holes at the end of the ligament.

When fixing covering material for injuries, no great tensile forces are required so that, therefore, other fixing means possibilities at the top of the implant post are conceivable. Thus, according to the invention, a magnet is located in the top of the implant post. The material to be fixed to the implant post can e simply fitted and equally easily detached again by means of a countermagnet. The same function is fulfilled by an adhesive surface for a velcro fastening, adhesive faces and other equivalent fixing possibilities.

Other advantages and features of the invention will be readily apparent from the following description of the preferred embodiments, the drawings and claims.

DESCRIPTION OF THE PREFERRED EMBODIMENTS

Figure 1:
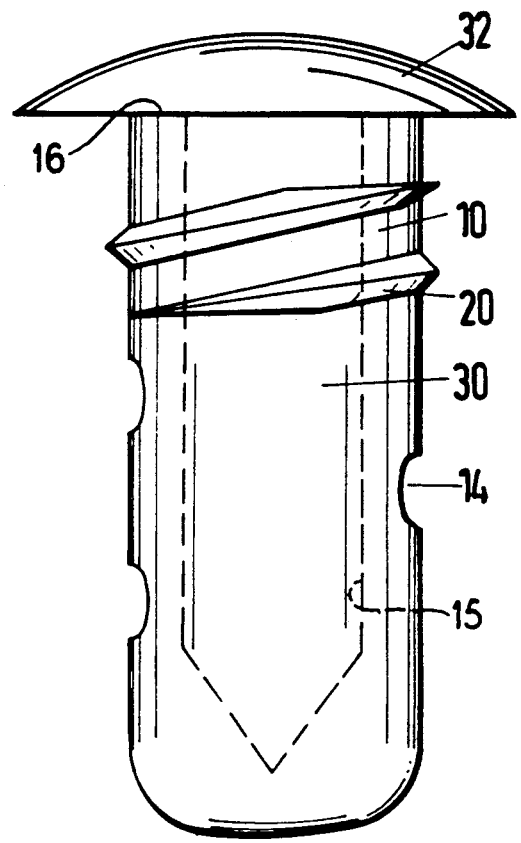
FIG. 1 is a side elevational view of a preferred embodiment of the inventive fixing device for use with artificial ligaments.

The principles of the present invention are particularly useful when incorporated in a fixing device illustrated in FIG. 1, which includes a basic or base element structure 10 having an axial bore 15 receiving an implant post 30.

The basic structure 10, which is to be screwed into a previously drilled hole in an exposed bone portion of the patient, can optionally consolidate therewith in an osseous manner as the bone tissue grows and engages the structure. The basic structure 10 is preferably made from a metal selected from titanium and titanium alloys and, on its outer surface, is either roughened by knurling or sandblasting or is coated with a tissue-friendly material, for example, hydroxyl apatite. In order to assist the osseous consolidation of the basic structure, it is possible to provide, on an outer cylindrical surface, cavities or depressions 14 which are also known as lacunae or breaks. This is particularly significant when using the inventive fixing device for artificial ligaments.

The bore 15 of the basic structure 10 is open at the top end or surface 16 and has an inner surface constructed so that the implant post 30 can be either screwed into the bore or inserted in a bayonet-like manner. The implant post 30 has a top 32 which forms fixing means is widened in a mushroom-shaped manner. Thus, after passing the implant post 30 through corresponding holes in the material to be fixed, such as, for example, fixing loops or holes, the top 32 will come into engagement with the material to hold it firmly.

Directly beneath the top end or surface 16, the basic structure is provided with a helix 20, which is illustrated as a thread with a 1.25 revolutions and a pitch or lead of 1.5. The surfaces forming the thread form an angle of 60° which will provide a sharp edge for penetrating into the bone material in a threadcutting manner.

Figure 2:
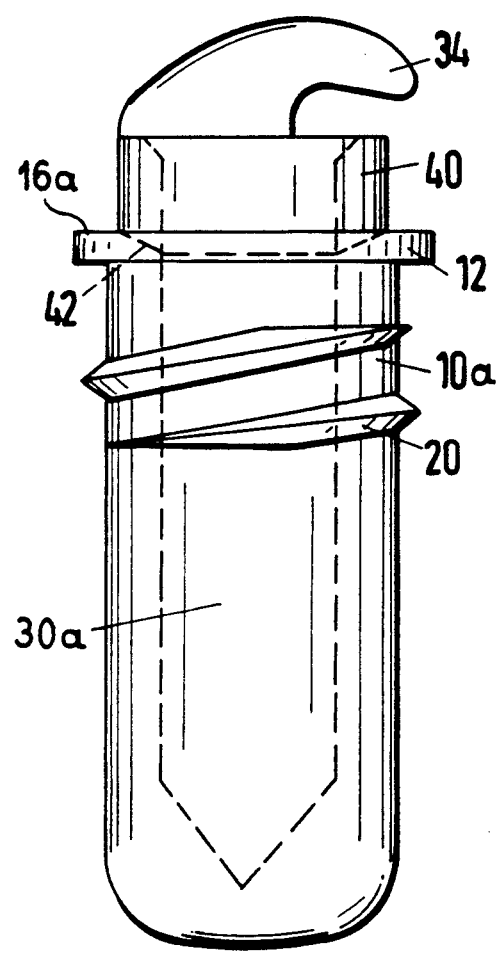
FIG. 2 is a side elevational view of another embodiment of the inventive fixing device also used with artificial ligaments and having an extension by a spacer sleeve.

An embodiment of the fixing device is illustrated in FIG. 2 and includes a basic structure or base element 10a, which has a bore receiving an implant post 30a. In this embodiment, a spacer sleeve 40 is provided. As illustrated, an upper surface or end 16a of the basic structure 10a has a countersunk portion 42 forming a cone-shape for receiving a cone-shaped edge of the spacer sleeve 40. In addition, the fixing means in the top part of the implant post 30a is constructed in the form of a hook 34, which, in the same way as a mushroom-shaped widened portion or top 32 of the post 30 of FIG. 1, is intended to engage with corresponding fixing loops or holes in the material to be fixed. As illustrated, the post 30a has a portion which holds the sleeve 40 on the basic structure. Also to prevent or limit the depth of insertion of the basic structure into the bone, the upper surface 16a is provided with a radially extending annular flange 12.

Figure 3:
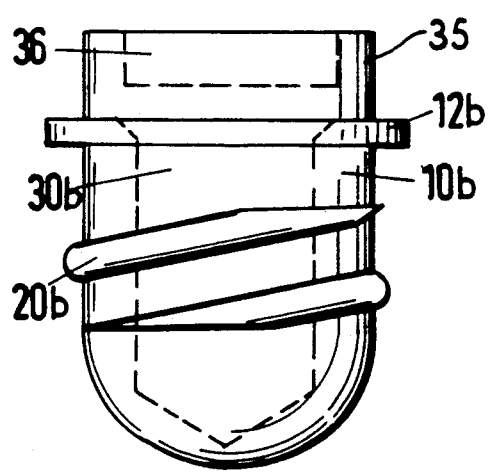
FIG. 3 is a side elevational view of yet another embodiment of the inventive fixing device for use to anchor covering material in the case of injuries.
Figure 4:
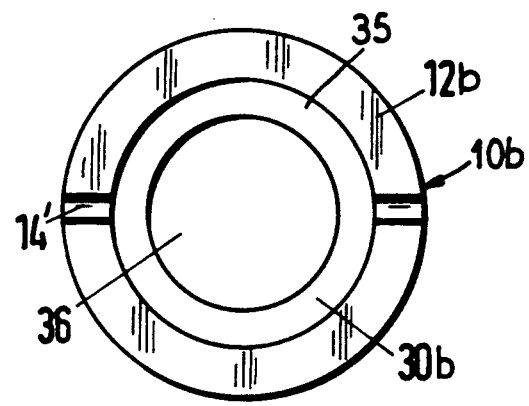
FIG. 4 is a top plan view of the embodiment of FIG. 3.

Another embodiment of the fixing device which is designed for fixing covering materials for injuries is illustrated in FIGS. 3 and 4. In this device, a basic structure 10b at a top end has a flange 12b which extends outward to prevent accidental excessively deep insertion of the basic structure 10b into a bone. The basic structure 10b is very short because it terminates directly below a helix 20b. The helix 20b, which has a thread of 1.25 revolutions and a pitch of 1.5 is, in this case, a rounded thread and, consequently, presses into the bone material in a thread-pressing manner. An implant post 30b has a top 35 which is provided with a magnet 36, which forms fixing means. The magnet 36 will interact with a corresponding countermagnet which is used for fixing the covering material for injuries and also various other types of materials, such as, for example, hair transplants.

As illustrated in FIG. 4, on the edges of the widened top or flange 12b of the basic structure 10b, it is possible to see blind bores 14' for the engagement of the special wrench required for the rapid installation or removal of the basic structure 10b. The top 35 of the implant post 30b is illustrated as having a circular configuration and receives a circular magnetic plate 36. It would be obvious to provide the above-mentioned other fixing possibilities, such as an adhesive surface for a velcro closure or an adhesive face on an upper surface of the top 35.

Although various minor modifications may be suggested by those versed in the art, it should be understood that I wish to embody within the scope of the patent granted hereon all such modifications as reasonably and properly come within the scope of my contribution to the art.

I claim:

1. An implantable fixing device for extraoral applications comprising an implant post and a basic structure, said basic structure having two ends and being implantable in a bone and having a cylindrical outer surface provided with a helix, said basic structure having an axial bore extending inward from one of the two ends of the basic structure, said implant post being connectible to the basic structure by having a portion inserted in said axial bore, said implant post having a fixing means for engaging material, said helix being arranged close to an upper edge of the one end of the basic structure and extending over a maximum of 1.5 revolutions on the basic structure with a pitch of between 1 and 2 so that the other end of the two ends of the structure is free of said helix, and an upper end of the bore having radially extending blind bores for receiving a special wrench for inserting and removing the basic structure.

2. An implantable fixing device according to claim 1, wherein the helix extends in a range of between 1 and 1.25 revolutions around the basic structure.

3. An implantable fixing device according to claim 1, wherein the helix has a pitch of 1.5.

4. An implantable fixing device according to claim 1, wherein the helix is a thread-cutting helix having surfaces forming a thread angle of approximately 60°.

5. An implantable fixing device according to claim 1, wherein the helix is a pressing helix having a thread with a rounded cross section.

6. An implantable fixing device according to claim 1, wherein the basic structure is made from a metal selected from a group consisting of titanium and titanium alloys.

7. An implantable fixing device according to claim 1, wherein the basic structure is provided with an external coat of a tissue-friendly material.

8. An implantable fixing device according to claim 7, wherein said coat is a plasma coating of hydroxyl apatite.

9. An implantable fixing device according to claim 1, wherein the basic structure is provided with means to limit the insertion into a bone, said means comprising a radially extending projection adjacent said one end of the basic structure.

10. An implantable fixing device according to claim 1, which includes a spacer sleeve being provided on said one end of the basic structure.

11. An implantable fixing device according to claim 10, wherein the basic structure has a conical countersink around the axial bore for receiving a conical portion of the spacer sleeve to mount the sleeve on said structure.

12. An implantable fixing device according to claim 10, wherein the spacer sleeve is made from an electrically insulating material.

13. An implantable fixing device according to claim 12, wherein said electrically insulating material is selected from a group consisting of aluminum oxide, magnesium oxide, zirconium dioxide, and combinations of aluminum oxide, magnesium oxide and zirconium dioxide.

14. An implantable fixing device according to claim 1, wherein the implant post and the bore have threads so that the implant post can be screwed into the bore of the basic structure.

15. An implantable fixing device according to claim 1, wherein the implant post and bore have means forming a bayonet connection therebetween so that the implant post is connected in the bore of said basic structure in a bayonet-like manner.

16. An implantable fixing device according to claim 1, wherein the implant post has radially extending blind bores on an upper end face.

17. An implantable fixing device according to claim 1, wherein the fixing means of the implant post is a widened head.

18. An implantable fixing device according to claim 1, wherein the fixing means of the implant post is at least one hook.

19. An implantable fixing device according to claim 1, wherein the fixing means of the implant post includes a recess receiving a magnet.

20. An implantable fixing device according to claim 1, wherein the fixing means of the implant post includes at least one adhesive surface for a velcro closure.

21. An implantable fixing device according to claim 1, wherein the fixing means of the implant post has at least one adhesive face.

22. An implantable fixing device according to claim 1, wherein the helix extends in a range of between 1 and 1.25 revolutions around the basic structure and which includes a spacer sleeve being provided on an upper surface of the basic structure.

23. An implantable fixing device according to claim 22, wherein the basic structure has a conical countersink around the axial bore for receiving a conical portion of the spacer sleeve to mount the sleeve on said structure.

24. An implantable fixing device according to claim 1, wherein the basic structure is closed at said other end.

* * * * *